United States Patent [19]
Roulier et al.

[11] Patent Number: 5,897,869
[45] Date of Patent: Apr. 27, 1999

[54] COSMETIC COMPOSITION IN THE FORM OF A SOFT PASTE AND PROCESS OF PREPARING IT

[75] Inventors: Véronique Roulier, Paris; Thérèse Daubige, Bray S/Seine, both of France

[73] Assignee: L'Oreal, Paris, France

[21] Appl. No.: 08/660,170

[22] Filed: Jun. 3, 1996

[30] Foreign Application Priority Data

Jun. 1, 1995 [FR] France .................................. 95 06537
Jul. 26, 1995 [FR] France .................................. 95 09107

[51] Int. Cl.$^6$ ........................... A61K 7/00; A61K 7/021; A61K 7/027; A61K 7/032
[52] U.S. Cl. ............................... 424/401; 424/63; 424/64; 424/69; 514/769; 514/770; 514/771; 514/784; 514/785; 514/786; 514/788.1
[58] Field of Search ............................... 424/401, 63, 69, 424/64; 514/784, 769, 770, 771, 785, 786, 788.1

[56] References Cited

U.S. PATENT DOCUMENTS

| | | | |
|---|---|---|---|
| 3,215,599 | 11/1965 | Thau et al. | 514/788.1 |
| 3,911,105 | 10/1975 | Papatoniou et al. | 424/64 |
| 4,164,563 | 8/1979 | Chang | 424/83 |
| 4,372,944 | 2/1983 | Herrold | 424/83 |
| 4,534,963 | 8/1985 | Gordon | 424/69 |
| 4,659,652 | 4/1987 | Arraudeau et al. | 424/63 |
| 4,871,536 | 10/1989 | Arraudeau | 424/59 |
| 5,437,859 | 8/1995 | Ser et al. | |
| 5,478,555 | 12/1995 | Bara et al. | |
| 5,510,107 | 4/1996 | Lecomte et al. | 424/401 |

FOREIGN PATENT DOCUMENTS

| | | | |
|---|---|---|---|
| 255655 | 2/1988 | European Pat. Off. | A61K 7/035 |
| 255843 | 2/1988 | European Pat. Off. | A61K 7/035 |
| 462032 | 12/1991 | European Pat. Off. | C08K 13/02 |
| 0 524 892 | 1/1993 | European Pat. Off. | |
| 0 530 084 | 3/1993 | European Pat. Off. | |
| 0 530 085 | 3/1993 | European Pat. Off. | |
| 0 655 234 | 5/1995 | European Pat. Off. | |
| 2715306 | 7/1995 | France | A61K 47/44 |

OTHER PUBLICATIONS

Chemical Abstracts, vol. 104, No. 2, Jan. 13, 1986, p. 301, abstract No. 10386 k.

*Primary Examiner*—Lynette F. Smith
*Assistant Examiner*—M K Zeman
*Attorney, Agent, or Firm*—Finnegan, Henderson, Farabow, Garrett & Dunner, L.L.P.

[57] ABSTRACT

The present application relates to an extruded cosmetic composition, provided in the form of a soft paste, comprising, in a fatty phase, at least one compound having a high melting temperature.

The invention also relates to a process for preparing the composition by extrusion.

7 Claims, No Drawings

COSMETIC COMPOSITION IN THE FORM OF A SOFT PASTE AND PROCESS OF PREPARING IT

The present invention relates to a cosmetic composition provided in the form of a soft paste, which can be used for the treatment of and/or as make-up for the lips and/or the skin.

The cosmetic compositions which can be applied to the skin or the lips as a make-up or treatment product, such as bases for the lips or lipsticks, generally contain fatty substances including waxes, pigments and/or fillers and, optionally, additives. It is known that the greater the quantity of waxes present in the composition, the firmer the consistency of the latter, which allows its use in the form of a stick. However, the presentation, in particular of a lipstick, in the form of a stick has certain disadvantages: the delineation of the contours of the lips is difficult and the heat-stability of the stick is not optimal.

Cosmetic compositions are also known which are provided in the form of a soft paste, applicable with the aid of a brush, for example. These compositions contain few or no waxes, which makes it possible to remove them and to apply them easily, given that a large quantity of waxes would lead to a composition of higher viscosity which would then be inapplicable.

However, waxes may prove to be cosmetically advantageous compounds. In particular, waxes having a high temperature at onset of melting, that is to say greater than about 100° C., can offer certain properties such as smoothness and slipperiness during application, as well as a nonsticky texture. They can also confer on the composition remarkable qualities of consistency, unctuousness and stability of the applied film. A problem arises when attempts are made to introduce these waxes, or other compounds having a high temperature at onset of melting, into a composition comprising, in addition, other fatty substances such as the waxes or oils commonly used in cosmetics. Indeed, when the entire mixture is heated to a temperature at which the high-melting waxes melt, denaturation of the other fatty substances present in the formula is observed, which denaturation consists in an oxidation of the said other fatty substances. It is thus not possible to obtain in this manner a composition of good quality.

In order to avoid this denaturation of the other fatty substances, it is possible to heat, in a first instance, the high-melting waxes to a temperature at which they melt, and then to introduce, in a second instance, at a lower temperature, the other fatty substances, waxes and oils. In this case, however, crystallization of the high-melting waxes is observed during the addition of the other fatty substances, hence the obtaining of a nonhomogenous mixture and of a final composition having a granular texture to the touch and/or on application which is incompatible with a satisfactory cosmetic use.

It is thus not therefore possible to obtain, by a prior art process, a cosmetic composition comprising a high-melting wax and having acceptable cosmetic qualities.

The aim of the present invention, therefore, is the production of such a composition and a process allowing the production of a cosmetic, especially anhydrous, composition of homogenous texture and cosmetically satisfactory, while containing fatty substances customarily used, such as waxes and/or oils, on the one hand, and compounds, especially waxes, having a high temperature at onset of melting, on the other hand.

One subject of the present invention is therefore an extruded composition provided in the form of a soft paste, comprising a fatty phase and at least one compound having a temperature at onset of melting at least equal to about 100° C. The term "about 100° C." is defined herein to mean 95° C.±5° C.

Another subject of the invention is a process for preparing this composition, in which, in a first stage, the compound having a temperature at onset of melting at least equal to about 100° C. is heated to a temperature T1 at which it melts; in a second stage, at least a first part of the other fatty substances is added and mixed at a temperature T2 at which they are molten without being degraded, while maintaining a degree of kneading; then the kneading of the mixture is continued during at least part of its cooling down to room temperature; the mixing and kneading operations being performed in at least one mixer-extruder.

"Temperature at onset of melting" is understood to mean in the present description the temperature at which the compound starts to melt.

This temperature can be determined especially by DTA (differential thermal analysis) which allows the obtaining of the thermogram (or melting curve) of the compound, especially of the wax, considered. The temperature at onset of melting corresponds to the temperature at which a notable change in slope can be observed on the thermogram. The melting point, for its part, represents the minimum point on the said thermogram.

In the remainder of the present description, the terms "compound having a temperature at onset of melting at least equal to about 100° C." and "high-melting compound" will be used interchangeably, to designate the compounds used within the framework of the present invention.

It has been observed that the composition according to the invention may comprise a large quantity of high-melting compounds, especially high-melting waxes, while remaining cosmetically satisfactory. The said composition has, moreover, a texture which is not very sticky, a good slipperiness on application and a good stability over time.

The composition according to the present invention is therefore a soft paste whose viscosity can be measured, in contrast to the solid structure of a stick, whose viscosity cannot be measured. The said dynamic viscosity at 25° C. is generally from 3 to 30 Pa.s, measured with a CONTRAVES TV rotational viscometer equipped with a rotor "MS-r4" at the frequency of 60 Hz.

The composition according to the invention therefore comprises at least one high-melting compound, whose temperature at onset of melting is at least equal to about 100° C., preferably greater than about 110° C.

Among these compounds, there may be mentioned waxes, polymers and plastic materials, as well as mixtures thereof.

Among the waxes, whose melting temperature is generally less than 150° C., there may be mentioned some polyethylene waxes, such as the wax "Polywax 2000T-6" from Petrolite (temperature at onset of melting: 125° C.), the wax "PED 191" from Hoechst (120° C.) and the wax "Epolene N-14" from Eastman Kodak (106° C.), alone or as a mixture.

These high-melting waxes may be the only waxes present in the composition, it being possible for the other fatty substances to be oils, gums and/or pasty compounds. They may also be combined with other waxes whose temperature at onset of melting is, for example, of the order of from 40 to 70° C. Among the polymers and plastic materials, whose melting temperature is generally greater than 150° C., and preferably less than 300° C., there may be mentioned polypropylenes, polyethylenes, PVCs, vinyl or acrylic polymers such as polystyrene, polyamides such as nylon, and mixtures thereof. These polymers or plastic materials may be optionally provided in powder or micronized form.

The high-melting compounds may generally be present in the composition according to the invention in an amount of from 2 to 50% by weight, preferably from 10 to 30%.

The composition according to the invention may therefore, in addition, comprise the fatty substances customarily used in cosmetics, especially silicone oils, gums and/or waxes, and/or vegetable, mineral, animal and/or synthetic oils and/or waxes, which are optionally volatile. These other fatty substances, as well as their quantities, may be chosen, without difficulty, by a persons skilled in the art on the basis of their general knowledge, so as to obtain a composition having the desired properties/qualities. In general, the remainder of the fatty phase may represent from 50 to 98% by weight of the composition, preferably from 70 to 90% by weight.

Among the waxes capable of being present in the composition according to the invention, there may be mentioned hydrocarbon waxes such as beeswax; Carnauba, Candellila, Ouricorury or Japan wax, waxes from sugar cane or cork fibres; lignite or paraffin waxes; microcrystalline waxes; lanolin wax; montan wax; ozokerites; polyethylene waxes; waxes obtained by Fischer-Tropsch synthesis; hydrogenated oils, fatty esters and glycerides which are concrete at 25° C. It is also possible to use silicone waxes, among which there may be mentioned alkyls, alkoxys and/or esters of polymethylsiloxane.

Among the oils capable of being present in the composition according to the invention, there may be mentioned hydrocarbon oils such as paraffin oil or petroleum jelly; perhydrosqualene; Arara oil; sweet almond, calophyllum, palm, castor, avocado, jojoba, olive or cereal germ oil; esters of lanolic acid, oleic acid, lauric acid or stearic acid; alcohols such as oleyl, linoleyl or linolenyl alcohol, isostearyl alcohol or octyl dodecanol. It is also possible to mention silicone oils such as PDMSs, optionally phenylated, such as phenyltrimethicones. It is also possible to use volatile oils such as cyclotetradimethylsiloxane, cyclopentadimethylsiloxane, cyclohexadimethylsiloxane, methylhexyldimethylsiloxane or isoparaffins.

The composition may also comprise a pulverulent phase which is generally present in an amount of from 0 to 40% by weight, preferably from 10 to 25% by weight, and which may comprise pigments and/or pearls and/or fillers normally used in cosmetic compositions.

The pigments may generally be present in the composition in an amount of from 0 to 30% by weight of the final composition, and preferably in an amount of from 5 to 20%. They may be white or colored, inorganic and/or organic. There may be mentioned, among the inorganic pigments, titanium, zirconium or cerium dioxides, as well as zinc, iron or chromium oxides, ferric blue. Among the organic pigments, there may be mentioned carbon black, barium, strontium, calcium or aluminium lacquers.

The pearls may be generally present in the composition in an amount of from 0 to 20% by weight, preferably at a high level of the order of from 5 to 15% by weight. Among the pearls which may be considered, there may be mentioned mica coated with titanium oxide, with iron oxide, with a natural pigment or with bismuth oxychloride as well as colored mica-titanium.

The fillers, which may generally be present in an amount of from 0 to 40% by weight, preferably from 10 to 25%, in the composition, may be inorganic or synthetic, lamellar or nonlamellar. There may be mentioned talc, mica, silica, kaolin, nylon and polyethylene powders, Teflon, starch, mica-titanium, natural pearl, boron nitrite, hollow microspheres such as Expancel (Nobel Industry), polytrap (Dow Corning) and microbeads of silcone resin (Tospearls from Toshiba, for example).

The composition may comprise, in addition, any additive normally used in the cosmetic field, such as antioxidants, perfumes, essential oils, preservatives, cosmetic active agents, moisturizers, vitamins, essential fatty acids, sphingolipids, sunscreens, surfactants, fat-soluble polymers such as polyalkylenes, especially polybutene, polyacrylates and silicone polymers compatible with the fatty substances. Of course, persons skilled in the art will be careful to choose this or these optional additional compounds, and/or their quantity, such that the advantageous properties of the composition according to the invention are not, or not substantially, damaged by the addition envisaged.

The compositions according to the invention may be provided in the form of a skin make-up or treatment product, in particular in the form of a foundation, a blusher or an eyeshadow, a lipstick or a treatment base for the lips, or alternatively of a treatment cream for the body or the face.

To prepare the composition according to the invention, in a first stage, the high-melting compound may be heated to a temperature T1 at which it is molten, while maintaining a degree of continuous kneading.

All or part of the other constituents of the composition, other than the fatty substances, which can be heated without being damaged at this temperature T1, may be optionally added as a mixture.

In a second stage, at least a first part of the fatty substances is added and mixed at a temperature T2, at which they are molten without being degraded, while maintaining a degree of kneading.

Preferably, T2 is of the order of the melting temperature of these fatty substances, and is less than T1.

It is also possible to add all or part of the constituents other than the fatty substances during this second stage.

This addition of the fatty substances and of the other constituents may be carried out in one or several stages. Thus, provision may be made for a third, or even fourth stage, which are similar to the second stage, in which there are added at T3, respectively T4, the fatty substances which have a similar melting temperature, optionally with the other constituents such as fillers or pigments. Preferably T3 is less than T2 and T4 is less than T3.

Finally, the kneading of the final mixture is continued during at least part of its cooling down to room temperature.

The process according to the invention is characterized by the mixing and kneading operations being performed in at least one mixer-extruder. The mixing and kneading operations are performed in at least one extruder.

Indeed, it was observed that the use of at least one mixer-extruder makes it possible to reproducibly obtain a paste of highly constant quality. Furthermore, it is possible, by adapting the outlet die of the mixer-extruder, to package the composition on-line at the outlet of the said die.

It is preferable to also perform the heating operations in a mixture-extruder.

It is also possible to perform the heating, mixing and kneading operations in several extruders, which may be placed one after the other. For example, heating may be conducted in an extruder A, mixing in an extruder B, and kneading in an extruder C. Further, heating and mixing could be conducted in an extruder A, and kneading in an extruder B.

However, a single twin-screw extruder is preferably used to perform the entire process.

The conditions under which the extrusion may be performed are described in Patent Application FR 94-00756, the disclosure of which is hereby incorporated into the present application by reference.

This process makes it possible to obtain a composition provided in the form of a soft and homogenous paste, although it contains high-melting compounds, optionally in a large quantity. Furthermore, the composition obtained after extrusion exhibits a special smoothness, and offers some sensation of slipperiness when it is applied to the skin, while avoiding the appearance and the sensation of oily fats.

The invention is illustrated in greater detail in, but not limited to, the following examples.

EXAMPLE 1

A treatment base was prepared which had the following composition:

| | |
|---|---|
| sesame oil | 35 g |
| lanolin | 35 g |
| "Epolene N-14" wax from Kodak | 15 g |
| talc | 15 g |

The composition was prepared in the following manner: the "Epolene N-14" wax was introduced into the first part of a twin-screw extruder, which was heated so that the wax melted (about 130° C.). The other constituents were introduced into a next part, at a temperature of the order of 85–90° C.

The outlet temperature was 30° C., the screw speed was 400 revolutions/min, and the residence time was about 2 minutes.

A soft paste with a viscosity equal to about 9 Pa.s was obtained at the outlet which was in the form of a single stable and homogenous phase, and which could be collected with the aid of a brush for its application.

This composition made it possible to obtain a homogenous film which could be easily applied and which could be spread easily and evenly.

This composition had a slippery and nonsticky feel, and it absolutely did not have a granular texture.

EXAMPLE 2

A lipstick was prepared which had the following composition:

| | |
|---|---|
| sesame oil | 45 g |
| isopropyl lanolate | 20 g |
| "Polywax 2000T-6" wax from Petrolite | 23 g |
| pigments and fillers | 12 g |

The composition was prepared according to Example 1.

An anhydrous soft paste with a viscosity of 12 Pa.s and a texture which was not very sticky was obtained which exhibited good slipperiness on application and good stability over time.

EXAMPLE 3

A treatment base was prepared which had the following composition:

| | |
|---|---|
| sesame oil | 35 g |
| lanolin | 35 g |
| "Epolene N-14" wax from kodak | 15 g |
| talc | 15 g |

The composition was mixed at 150° C. with the aid of a Moritz type turbine and cooled. A heterogeneous paste of granular texture was obtained.

What is claimed is:

1. A process for preparing a soft paste composition comprising a fatty phase containing at least one fatty substance and at least 10% by weight of at least one wax having a temperature at onset of melting at least equal to 95° C., said at least one wax being different from said at least one fatty substance, said process comprising the steps of:

in a first stage, heating said at least one wax having a temperature at onset of melting at least equal to 95° C. to a temperature T1 until it melts, in a second stage,
      adding at least some of the at least one fatty substance making up said fatty phase to the melted wax obtained in the first stage,
      mixing and kneading at a temperature T2 to form a mixture which is molten without being degraded, and in a final stage, cooling said mixture down to room temperature, and continuing kneading of the mixture during at least part of its cooling down to room temperature whereby the composition formed is a soft paste, and wherein said mixing and kneading steps are performed in at least one mixer-extruder.

2. A process according to claim 1, wherein constituents of said composition other than said at least one fatty substance are added during the first stage, the second stage, or during both stages.

3. A process according to claim 1, wherein said heating step is performed in a mixer-extruder.

4. A process according to claim 1, wherein said heating, mixing and kneading steps are performed in more than one extruder.

5. A process according to claim 1, wherein said heating, mixing and kneading steps are performed in a twin-screw extruder.

6. A process according to claim 1, said process further comprising:

in a third stage, between said second stage and said final stage, adding at least part of the remaining at least one fatty substance, which was not added in the second stage, to the melted compound obtained in the first stage and mixing and kneading at a temperature T3 to form a mixture which is molten without being degraded.

7. A process according to claim 6, said process further comprising:

in a fourth stage, between said third stage and said final stage, adding the remaining at least one fatty substance, which was not added in the third stage, to the melted compound obtained in the first stage and mixing and kneading at a temperature T4 to form a mixture which is molten without being degraded.

* * * * *